(12) United States Patent
Sagalowicz et al.

(10) Patent No.: US 11,109,615 B2
(45) Date of Patent: Sep. 7, 2021

(54) VITAMIN A COMPOSITION (71) Applicant: NESTEC S.A., Vevey (CH)

(72) Inventors: Laurent Sagalowicz, Blonay (CH);
Charlotte Gancel, Lausanne (CH);
Cyril Moccand, Lausanne (CH);
Isabelle Martiel, Zurich (CH)

(73) Assignee: Societe des Produits Nestle S.A., Vevey (CH)

( * ) Notice: Subject to any disclaimer, the term of this patent is extended or adjusted under 35 U.S.C. 154(b) by 153 days.

(21) Appl. No.: 15/548,163

(22) PCT Filed: Feb. 10, 2016

(86) PCT No.: PCT/EP2016/052770
§ 371 (c)(1),
(2) Date: Aug. 2, 2017

(87) PCT Pub. No.: WO2016/128428
PCT Pub. Date: Aug. 18, 2016

(65) Prior Publication Data
US 2018/0007946 A1    Jan. 11, 2018

(30) Foreign Application Priority Data

Feb. 11, 2015 (EP) .................................... 15154595

(51) Int. Cl.
*A23L 33/155* (2016.01)
*A23L 29/10* (2016.01)
(Continued)

(52) U.S. Cl.
CPC ............ *A23L 33/155* (2016.08); *A23L 27/20* (2016.08); *A23L 29/10* (2016.08); *A23L 33/105* (2016.08);
(Continued)

(58) Field of Classification Search
None
See application file for complete search history.

(56) References Cited

U.S. PATENT DOCUMENTS

| 5,728,681 A | * | 3/1998 | Kido | ................... A61J 1/2093 514/167 |
| 2003/0198727 A1 | * | 10/2003 | Koike | ................... A61K 31/56 426/601 |

(Continued)

FOREIGN PATENT DOCUMENTS

| CN | 1128946 A | 8/1996 |
| CN | 1150757 A | 5/1997 |

(Continued)

OTHER PUBLICATIONS

USAID: Fortification Basics: Stability; published online at least by Dec. 30, 2013 at: https://www.dsm.com/content/dam/dsm/nip/en_US/documents/stability.pdf (Year: 2013).*

(Continued)

*Primary Examiner* — Patricia A George
(74) *Attorney, Agent, or Firm* — K&L Gates LLP (57) ABSTRACT

The present invention relates to a composition comprising triglycerides, surfactant, self-assembled structures and vitamin A or provitamin A. Further aspects of the invention are a food product, the use of a composition comprising triglycerides, surfactant and self-assembled structures to stabilize vitamin A or provitamin A and a process for preparing a stabilized vitamin A or provitamin A composition.

11 Claims, 9 Drawing Sheets

(51) Int. Cl.
  A61K 47/14    (2017.01)
  A23L 33/105   (2016.01)
  A23L 27/20    (2016.01)
  A61K 9/107    (2006.01)
  A61K 31/07    (2006.01)
  A61K 47/22    (2006.01)
  A61K 47/24    (2006.01)
  A61K 9/127    (2006.01)

(52) U.S. Cl.
  CPC .............. *A61K 9/107* (2013.01); *A61K 31/07* (2013.01); *A61K 47/14* (2013.01); *A23V 2002/00* (2013.01); *A61K 9/1075* (2013.01); *A61K 9/1274* (2013.01); *A61K 47/22* (2013.01); *A61K 47/24* (2013.01)

(56) References Cited

U.S. PATENT DOCUMENTS

| | | | |
|---|---|---|---|
| 2004/0191263 A1* | 9/2004 | Hageman | A23K 50/10 424/184.1 |
| 2005/0008686 A1 | 1/2005 | Mannino et al. | |
| 2008/0217280 A1* | 9/2008 | Dekker | B65D 81/3283 215/6 |
| 2010/0119600 A1* | 5/2010 | Opheim | A61K 9/4858 424/456 |

FOREIGN PATENT DOCUMENTS

| | | |
|---|---|---|
| CN | 1313753 A | 9/2001 |
| CN | 101278890 | 10/2008 |
| CN | 101686700 A | 3/2010 |
| DE | 19831798 | 1/2000 |
| EP | 1905425 | 4/2008 |
| EP | 1905425 A1 | 4/2008 |
| GB | 2379386 | 3/2003 |
| JP | 2010001218 | 1/2010 |
| TW | 200824717 A | 6/2008 |
| WO | 9531969 | 11/1995 |

OTHER PUBLICATIONS

MM: Mohamed Mathlouthi: Water content, water activity, water structure and the stability of foods; Food Control: vol. 12, 2001, p. 409-417. (Year: 2001).*
Clum: Skin care compositions; published Dec. 29, 1993 as EP 0440398. (Year: 1993).*
Lee: Cosmetic material containing triple-encapsulated retinol; published Jan. 30, 2002 as GB2379386. (Year: 2002).*
Liang: Micellar Systems Useful for Delivery of Lipophilic or Hydrophobic Compounds; EP 1706098; Published: Oct. 4, 2006. (Year: 2006).*
Mayer: Behavior of vitamin E acetate delivery systems under simulatedgastrointestinal conditions: Lipid digestion and bioaccessibilityof low-energy nanoemulsions; Journal of Colloid and Interface Science 404 (2013) 215-222. (Year: 2013).*
Hernandez: Lipid Nutraceuticals Give Fats A Good Name; published Jul. 1, 2003 (Year: 2003).*
Sutton: The Effects of Soya Lecithin on the Absorption, Utilization and Storage of Vitamin a and Carotene in the white Rat; The Journal of Nutrition, vol. 36, Issue 3, Sep. 1948, pp. 391-404; published: Sep. 1, 1948 (Year: 1948).*
Fontana, Jr. et al. "Water Activity Values of Select Consumer and Pharmaceutical Products" Sep. 25, 2007, Blackwell Publishing Ltd, pp. 421-422, XP055180891.
Schmidt et al. "Water Activity Values of Select Food Ingredients and Products" Sep. 25, 2007, Blackwell Publishing Ltd, pp. 407-420, XP055180892.
Nagarsekar et al."Electron Microscopy and Theoretical Modeling of Cochleates" Langmuir, 2014, vol. 30, 13143-13151.
Sagalowicz et al. "Delivery systems for liquid food products" Current Opinion in Colloid & Interface Science, 2010, vol. 15, pp. 61-72.
Chinese Office Action for Appl. No. 201680008775.0 dated Apr. 28, 2020.

* cited by examiner

VITAMIN A COMPOSITION

CROSS REFERENCE TO RELATED APPLICATIONS

The present application is a National Stage of International Application No. PCT/EP2016/052770, filed on Feb. 10, 2016, which claims priority to European Patent Application No. 15154595.1, filed on Feb. 11, 2015, the entire contents of which are being incorporated herein by reference.

FIELD OF THE INVENTION

The present invention relates to a composition comprising triglycerides, surfactant, self-assembled structures and vitamin A or provitamin A. Further aspects of the invention are a food product, the use of a composition comprising triglycerides, surfactant and self-assembled structures to stabilize vitamin A or provitamin A and a process for preparing a stabilized vitamin A or provitamin A composition.

BACKGROUND OF THE INVENTION

Vitamin A is one of the four micronutrients with the highest deficiencies worldwide, the others being iron, zinc and iodine. It is estimated that 600,000 children under the age of 5 die each year due to vitamin A deficiency [Black, R. E., et al., Lancet, 371(9608), 243-60 (2008)]. For this target population, vitamin A is believed to be the micronutrient for which a deficiency causes the highest number of fatalities. Vitamin A deficiency also affects adults, especially pregnant women. First symptoms are night blindness and a decreased efficiency of the immune system. Vitamin A deficiencies occur principally in developing countries due to diets low in vitamin A or provitamin A (a substance converted to vitamin A within the body).

Food fortification is one method to increase vitamin A intake along with dietary diversification. Unfortunately fortification of foods with vitamin A or provitamin A is not straightforward. Vitamin A is susceptible to oxidation and isomerization, with large losses of vitamin A activity occurring during processing, transportation and storage of fortified foods. Vitamin A may further be destroyed if the fortified foods are to be cooked, for example by boiling. Adding vitamin A at levels above the intended fortification level to compensate for loses is undesirable because of the potential for overdosing [S. M. Loveday et al., Trends in Food Science & Technology 19, 657-668 (2008)]. Vitamin A is accumulated in the adipose tissue and high levels are acutely toxic. Over-dosing the amount of vitamin A in products also adds cost. Food products providing vitamin A in developing countries must be affordable in order to be obtainable by those in need. It would therefore be desirable to provide a stabilized form of vitamin A or provitamin A, especially one which can safely be consumed.

EP1418822 describes stabilizing a fat-soluble vitamin such as vitamin A in a solid vegetable fat and a matrix of protein which is cross-linked with a reducing substance. However such matrixes are complicated to produce and may be expensive.

U.S. Pat. No. 5,994,318 describes incorporating vitamin A in nanocochleates to enhance stability. The manufacturing process involves the use of organic solvents such as chloroform.

U.S. Pat. No. 2,827,452 describes stabilizing vitamin A with complex-forming starches and dextrins.

There remains a need to provide further approaches for stabilizing vitamin A, particularly stabilizing systems which do not require expensive manufacturing processes and which can be formed from ingredients having a natural source. Existing stabilizing systems may give good stability at low water activity, but offer little protection at higher water activities.

An object of the present invention is to improve the state of the art and to provide an improved solution to overcome at least some of the inconveniences described above, or at least to provide a useful alternative. The object of the present invention is achieved by the subject matter of the independent claims. The dependent claims further develop the idea of the present invention. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

The present invention provides in a first aspect a composition comprising triglycerides, surfactant, self-assembled structures and vitamin A or provitamin A. In a second aspect, the invention relates to a food product comprising the composition comprising triglycerides, surfactant, self-assembled structures and vitamin A or provitamin A. A third aspect of the invention relates to the use of a composition comprising triglycerides, surfactant and self-assembled structures to stabilize vitamin A or provitamin A. A still further aspect of the invention is a process for preparing a stabilized vitamin A or provitamin A composition comprising the steps; providing triglycerides, surfactant and vitamin A or provitamin A all in a liquid state, and mixing the triglycerides, surfactant and vitamin A or provitamin A to form a stabilized composition, wherein the surfactant is present at a level of between 0.1 and 30 wt. % in the triglycerides.

It has been surprisingly found by the inventors that vitamin A in oil is stabilized by the presence of lecithin and self-assembled structures. This increased stability is maintained even in high water activity environments, such as an $A_w > 0.5$. For example, a solution of 0.33% vitamin A palmitate in palm oil stored at 60° C. and 68% RH was found to be completely degraded after 60 days when reversed micelles and 3.7 wt. % lecithin were present in the solution, whereas the same solution without reversed micelles and lecithin degraded after only 30 days. In a similar palm oil system at 40° C./68% RH, 75° C./50% RH and 80° C./68% RH, lecithin and self-assembled structures were found to be more effective at stabilizing vitamin A than BHT (butylated hydroxytoluene), a commonly used antioxidant. Without wishing to be bound by theory, the inventors believe that lecithin self-assembled structures concentrate free radicals and pro-oxidants such as metals, enclosing them and so separating them from vitamin A dissolved in the triglycerides.

DETAILED DESCRIPTION OF THE INVENTION

Consequently the present invention relates in part to a composition comprising triglycerides, surfactant, self-assembled structures and vitamin A or provitamin A. The composition may comprise triglycerides, surfactant, self-assembled structures, vitamin A and provitamin A. The triglycerides comprised in the composition of the invention may for example be provided as any oils or fats commonly used in the food industry. The triglycerides may be provided as oils or fats derived from vegetable material or from animal milk. For example, the triglycerides may be obtained from a material selected from the group consisting of palm oil, sunflower oil, rapeseed oil, olive oil, palm kernel oil, coconut oil, cocoa butter, illipe, sal, shea, bovine milk fat and combinations of these. The triglycerides may be fractionated or interesterified oils and fats.

Surfactants are compounds that lower the interfacial tension between two liquids, for example between a lipid and an aqueous phase. The term 'self-assembled' refers to the spontaneous formation of associates or sub-micrometer structures by separate molecules. Molecules in self-assembled structures find their appropriate location based solely on their structural and chemical properties due to given intermolecular forces, such as hydrophobic, hydration, phase segregation or electrostatic forces [Evans, D. F.; Wennerstrom, H. (Eds.); 'The Colloidal Domain', Wiley-VCH, New York, (1999)]. The result of self-assembly does not depend on the process of preparation itself and corresponds to a state of minimum energy (stable equilibrium) of the system.

Vitamin A is the name of a group of fat-soluble retinoids, including retinol, retinal, retinoic acid, and retinyl esters. Vitamin A is involved in immune function, vision, reproduction, and cellular communication. Vitamin A also supports cell growth and differentiation, playing a critical role in the normal formation and maintenance of the heart, lungs, kidneys, and other organs. Two forms of vitamin A are available in the human diet: preformed vitamin A (retinol and its esterified form, retinyl ester) and provitamin A. Preformed vitamin A is found in foods from animal sources, including dairy products, fish, and meat (especially liver). By far the most important provitamin A is beta-carotene; other types of provitamin A are alpha-carotene and beta-cryptoxanthin. The body converts these plant pigments into vitamin A. Both provitamin A and preformed vitamin A must be metabolized intracellularly to retinal and retinoic acid, the active forms of vitamin A, to support the vitamin's important biological functions [National Institutes of Health factsheet, retrieved 15 Jan. 2015, ods.od.nih.gov/factsheets/VitaminA-HealthProfessional]. The vitamin A in the composition of the current invention may be vitamin A palmitate or vitamin A acetate.

The composition of the present invention may be used in many forms, for example it may be applied to the skin as a dermatological preparation. It is particularly advantageous that the composition of the present invention may be an edible composition, and so may for example provide stabilized vitamin A to be consumed orally. The term "edible" refers to substances which can be eaten safely. Whilst the current invention is not limited to substances permitted for consumption in any particular jurisdiction, edible compositions may for example comprise materials approved for human consumption by the U.S. Food and Drug Administration.

At least part of the vitamin A or provitamin A may be dissolved in the triglycerides comprised within the composition of the invention. For example, substantially all the vitamin A or provitamin A may be dissolved in the triglycerides.

The surfactant comprised within the composition of the invention may be selected from the group consisting of monoglycerides, phospholipids, galactolipids, polyoxyethylene sorbitan fatty acid esters and combinations of these. The surfactant comprised within the composition of the invention may be selected from the group consisting of monoglycerides, phospholipids, galactolipids and combinations of these. The surfactant may be in the form of self-assembled structures in the oil phase of the composition of the invention. In order to form self-assembled structures in the oil phase, the surfactant concentration must be greater than the CMC (critical micellar concentration) in the oil phase triglyceride composition. Below this concentration, no self-assembled structures are formed. The self-assembled structures in the composition of the invention may comprise the surfactant. The surfactant may be present at a level of between 0.1 and 30 wt. % in the triglycerides, for example between 0.2 and 25 wt. % in the triglycerides, for example between 0.5 and 20 wt. % in the triglycerides, for further example between 1 and 3.0 wt. % in the triglycerides, for still further example between 2 and 8 wt. % in the triglycerides. The self-assembled structures may be present at a level of at least 0.05 wt. % in the composition. The surfactant may be monoglycerides. The surfactant may be phospholipids. The phospholipids may be derived from a vegetable source, such as soy, canola, rapeseed, sunflower, wheat, or oat; or an animal source such as egg. Phospholipids derived from soy and canola are commercially available, e.g. as soy lecithin and canola lecithin. The phospholipids may be phosphatidylcholine, a component, for example, of lecithin. The total vitamin A and provitamin A present in the composition may be at least 0.1 wt. %, for example at least 0.2 wt. %, for further example at least 0.4 wt. %. The stability of vitamin A has been found to increase as the ratio of triglyceride to vitamin A increases. The total level of vitamin A and provitamin A present in the triglycerides of the composition may be at least 0.1 wt. % for example at least 0.2 wt. %, for further example at least 0.3 wt. %.

The self-assembled structures comprised within the composition of the invention may be selected from the group consisting of L2 phase, reversed microemulsion, reversed micellar cubic structure, reversed bicontinuous cubic structure, reversed sponge phase, reversed hexagonal structure, lamellar phase and combinations of these.

In an embodiment of the invention where the self-assembled structures comprised within the composition of the invention are lamellar phase (for example the lamellar liquid-crystalline phase), the lamellar phase may contain a limited amount of water and a large content of oil and be distinct from vesicles, liposomes or cochleates. For example the composition of the invention may comprise lamellar phase self-assembled structures and water; the weight of water being less than 3.0% (for example less than 4%) of the total weight of triglycerides, surfactant, vitamin A and water; and the weight of triglycerides may be at least 50% (for example at least 80%) of the total weight of triglycerides, surfactant, vitamin A and water.

The self-assembled structures comprised within the composition of the invention may be selected from the group consisting of L2 phase, reversed microemulsion, reversed micellar cubic structure, reversed bicontinuous cubic structure, reversed sponge phase, reversed hexagonal structure and combinations of these. The self-assembled structures may be composed of reversed micelles or reversed hexagonal structures. The self-assembled structures may be composed of reversed micelles. The terminology for the different self-assembled structures is used in the conventional sense, as described by Sagalowicz [L. Sagalowicz et al., Trends in Food Science and Technology 17, 204-214 (2006).] Another article describing self-assembly structures is Yaghmur [Yaghmur, A. et al. *Langmuir*, 22, 517-521 (2006)]

The presence of self-assembled structures and their nature can be determined by the use of small angle X-ray scattering.

The composition of the invention may further comprise an antioxidant. Antioxidants may further enhance the stability of vitamin A. In the present invention the term "antioxidant" is understood to include any one or more of various substances that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include coenzyme Q10 ("CoQ10"), flavonoids, glutathione Goji (wolfberry), hesperidine, lactowolfberry, lignan, lutein, lycopene, polyphenols, selenium, vitamin B1, vitamin B6, vitamin B12, vitamin C, vitamin D, vitamin E, zeaxanthin, synthetic antioxidants, citric acid or combinations thereof. The antioxidant may be selected from the group consisting of ascorbyl palmitate, rosemary extract, citric acid, green tea extract, tocopherol, butylated hydroxytolulene (BHT), butylated hydroxyanisole (BHA), tert-butylhydroquinone (TBHQ) and combinations of these. The antioxidant may be selected from the group consisting of ascorbyl palmitate, rosemary extract, citric acid, green tea extract, butylated hydroxytolulene (BHT), butylated hydroxyanisole (BHA), tert-butylhydroquinone (TBHQ) and combinations of these. The antioxidant in the composition of the invention may be selected from the group consisting of rosemary extract, green tea extract, a butylated phenol (for example BHT) and combinations of these. The antioxidant in the composition of the invention may be a mixture of green tea extract and rosemary extract. The antioxidant in the composition of the invention may be rosemary extract. The antioxidant in the composition of the invention may be a butylated phenol, for example butylated hydroxytolulene (BHT), butylated hydroxyanisole (BHA), tert-butylhydroquinone (TBHQ). The antioxidant may be butylated hydroxytolulene. It has surprisingly been found that compositions comprising triglycerides, surfactant, self-assembled structures and butylated phenol antioxidants are particularly effective at protecting vitamin A or provitamin A when it is desired to protect the vitamin A or provitamin A both during shelf-life and also under high moisture home-cooking conditions such as simmering. For example, a model system simulating a concentrated vitamin A-containing bouillon which comprised triglycerides and lecithin self-assembled structures was prepared. Adding BHT or -tocopherol to this system had a similar but small effect on the stability of vitamin A during long term storage at low moisture conditions. (The system having lecithin self-assembled structures without antioxidants already had good stability.) However, when the model systems were boiled (to simulate the use of the bouillon in cooking), vitamin A in the BHT-containing system was much more stable than vitamin A in the system containing -tocopherol.

It has surprisingly been found that compositions comprising triglycerides, surfactant, self-assembled structures and green tea extract and/or rosemary extract are particularly effective at protecting vitamin A or provitamin A when it is desired to protect the vitamin A or provitamin A both during shelf-life and also under high moisture home-cooking conditions such as simmering. For example, a model system simulating a concentrated vitamin A-containing bouillon which comprised triglycerides and lecithin self-assembled structures was prepared. Adding green tea extract, rosemary extract or -tocopherol to this system had only a small effect on the stability of vitamin A during long term storage at low moisture conditions. (The system having lecithin self-assembled structures without antioxidants already had good stability.) However, the inventors were surprised to find that when the model systems were boiled (to simulate the use of the bouillon in cooking), vitamin A in the system containing green tea extract or rosemary extract was much more stable than vitamin A in the system without added antioxidants or in systems containing -tocopherol.

The composition of the invention may further comprise water. It is beneficial that the composition of the invention provides good vitamin A and provitamin A stability in systems with appreciable levels of moisture such as are commonly found in food products. The composition may further comprise water and have a water activity greater than 0.3, for example greater than 0.4, for further example greater than 0.45, for further example greater than 0.50. The composition may have a water activity between 0.3 and 0.99, for example between 0.4 and 0.95. In the context of the present invention the term water activity is defined in the manner common in food science $$A_w = \frac{P}{P_0}$$

where $A_w$ is the water activity, P is the vapour pressure of water in the food and $P_0$ is the vapour pressure of pure water at the same temperature [Wiley Encyclopedia of Food Science and Technology, $2^{nd}$ Edition, 2614 (2000)]. The composition of the invention may have a water content between 0.001 wt. % and 30 wt. % of the total weight of triglycerides, surfactant, vitamin A and water, for example between 0.01 wt. % and 20 wt. % of the total weight of triglycerides, surfactant, vitamin A and water, for example between 0.05 wt. % and 10 wt. % of the total weight of triglycerides, surfactant, vitamin A and water, for further example between 0.05 wt. % and 4 wt. % of the total weight of triglycerides, surfactant, vitamin A and water. Such water contents are particularly good for ensuring the optimum self-assembly structure to prevent vitamin A degradation.

The composition of the invention may have a triglyceride content of at least 50% of the total weight of triglycerides, surfactant, vitamin A and water; for example at least 80% of the total weight of triglycerides, surfactant, vitamin A and water, for example at least 90% of the total weight of triglycerides, surfactant, vitamin A and water.

In a further aspect, the composition of the invention may be comprised within a food product. As previously discussed, it is beneficial to be able to provide a food product containing vitamin A or provitamin A where the vitamin or provitamin is stable during storage. The total vitamin A and provitamin A present in the food product may be at least 0.002 wt. %, for example at least 0.005 wt. %, for further example at least 0.01 wt. %. The food product of the invention may be a concentrated bouillon, a taste maker, a pasta or noodle product, a soup, a sauce, a dairy product, a breakfast cereal, a milk powder, a beverage, a nutritional supplement or a pet food. The food product of the invention may for example be a concentrated bouillon, a taste maker, a pasta or noodle product, a breakfast cereal, a milk powder, a nutritional supplement or a pet food. Concentrated bouillons, taste makers and sauces provide a good vehicle for food fortification in a target population as they are relatively inexpensive and may be used in many different meals. The food product of the invention may be a concentrated bouillon. The concentrated bouillon comprising the composition of the invention may be a soft concentrated bouillon or hard concentrated bouillon, e.g. a bouillon cube. The composition of the invention may be comprised within the oil component of a concentrated bouillon, for example with antioxidants such as BHT.

The composition of the invention provides vitamin A or provitamin A which is stable in the presence of water. The food product comprising the composition of the invention may have a water activity greater than 0.3, for example greater than 0.4, for further example greater than 0.45, for further example greater than 0.50. The food product may have a water activity between 0.3 and 0.99, for example between 0.4 and 0.95. The food product comprising the composition of the invention may have a water content between 0.001 wt. % and 30 wt. %, for example between 0.01 wt. % and 20 wt. %, for example between 0.05 wt. % and 10 wt. %, for further example between 0.05 wt. % and 4 wt. %.

In a further aspect the invention provides the use of a composition comprising triglycerides, surfactant and self-assembled structures to stabilize vitamin A or provitamin A. At least part of the vitamin A or provitamin A may be dissolved in the triglycerides in the composition used according to the invention. The self-assembled structures comprised within the composition used according to the invention may be selected from the group consisting of L2 phase, reversed microemulsion, reversed micellar cubic structure, reversed bicontinuous cubic structure, reversed sponge phase, reversed hexagonal structure, lamellar phase and combinations of these. The self-assembled structures comprised within the composition used according to the invention may be selected from the group consisting of L2 phase, reversed microemulsion, reversed micellar cubic structure, reversed bicontinuous cubic structure, reversed sponge phase, reversed hexagonal structure and combinations of these. The self-assembled structures may be composed of reversed micelles or reversed hexagonal structures.

The surfactant in the composition used according to the invention may be selected from the group consisting of monoglycerides, galactolipids, phospholipids, polyoxyethylene sorbitan fatty acid esters and combinations of these. The surfactant in the composition used according to the invention may be in the form of self-assembled structures in the oil phase of the composition. The surfactant may be present at a level of between 0.1 and 30 wt. % in the triglycerides, for example between 0.2 and 25 wt. % in the triglycerides, for example between 0.5 and 20 wt. % in the triglycerides, for further example between 1 and 3.0 wt. % in the triglycerides, for still further example between 2 and 8 wt. % in the triglycerides. The surfactant may be phospholipids.

The composition used according to the invention may further comprise antioxidants, for example butylated hydroxytoluene. The antioxidant in the composition used according to the invention may be selected from the group consisting of rosemary extract, green tea extract, a butylated phenol (for example BHT) and combinations of these. The antioxidant may be a mixture of green tea extract and rosemary extract. The antioxidant may be rosemary extract. The composition used according to the invention may have a water activity greater than 0.3, for example greater than 0.4, for further example greater than 0.45, for further example greater than 0.50. The composition used according to the invention may have a water activity between 0.3 and 0.99, for example between 0.4 and 0.95.

The composition comprising triglycerides, surfactant and self-assembled structures may be used to stabilize vitamin A or provitamin A in a food product. The composition comprising triglycerides, surfactant and self-assembled structures may be used to stabilize vitamin A or provitamin A in a food product during shelf life and during cooking, for example cooking by heating the food product in contact with water at a temperature greater than 70° C. The food product may be a concentrated bouillon or taste maker. Shelf life is the recommended length of time that food products and other perishable items can be stored, during which the defined quality of a specified proportion of the goods remains acceptable under expected (or specified) conditions of distribution, storage and display.

In a still further aspect, the invention provides a process for preparing a stabilized vitamin A or provitamin A composition comprising the steps; providing triglycerides, surfactant and vitamin A or provitamin A all in a liquid state, and mixing the triglycerides, surfactant and vitamin A or provitamin A to form a stabilized composition, wherein the surfactant is present at a level of between 0.1 and 30 wt. % in the triglycerides, for example the surfactant may be present at a level of between 0.2 and 25 wt. % in the triglycerides, for example at a level of between 0.5 and 20 wt. % in the triglycerides, for further example at a level of between 1 and 3.0 wt. % in the triglycerides, for still further example between 2 and 8 wt. % in the triglycerides. The surfactant may be phospholipids. The surfactant, vitamin A or provitamin A may be dissolved in the triglycerides. The stabilized composition may further be added to other food ingredients to form a food product.

Those skilled in the art will understand that they can freely combine all features of the present invention disclosed herein. In particular, features described for the product of the present invention may be combined with the process of the present invention and vice versa. Further, features described for different embodiments of the present invention may be combined. Where known equivalents exist to specific features, such equivalents are incorporated as if specifically referred to in this specification. Further advantages and features of the present invention are apparent from the figures and non-limiting examples.

EXAMPLES

Example 1: Degradation of Vitamin A in Oil with Varying Lecithin Content

Palm oil (SUNIA), soy lecithin (Cargill) and vitamin A palmitate (DSM) were heated in an oven at 60°. Vitamin A palmitate was not held above 60° C. for longer than 5 minutes to avoid possible degradation. The oil was mixed with lecithin in a 1 liter Schott bottle and then stirred for 10 minutes in a 50° C. water bath. Vitamin A palmitate was then added and the mixture was homogenized by using magnetic stirring for 15 minutes in a 50° C. water bath. Initial vitamin A palmitate content was 0.33% (a vitamin A content of 0.18 wt. %), lecithin content was varied between 0% and 15%. The total amount of lipid was 500 g. 5 g of the mixture was then transferred to a small crystallizing dish. Samples corresponding to $T_0$ of the storage test were directly frozen before any heat treatment and were used to determine the initial value of vitamin A. All initial values obtained were in the expected range (5% uncertainty). The other samples were used for storage tests.

For the storage tests, the crystallizing dishes were transferred into a climatic chamber regulated at 60° C. and 68% relative humidity, before being analyzed. Vitamin A analysis was performed by UPLC. Before proceeding with chromatography, the solution containing vitamin A was subjected to a hot saponification step for 30 minutes at 85° C. in ethanol with 7 g potassium hydroxide, followed by solid phase extraction using 100 mL n-hexane for elution. Solvent was evaporated using a rotary evaporator and extract dissolved in 5 mL n-hexane was injected to the UPLC for vitamin A analysis. Chromatography was performed with an Acquity UPLC BEH HILIC 1.7 µm 2.1×100 mm analytical column in normal phase at 1.2 mL/min, using 1% 2-propanol in n-hexane as mobile phase. Vitamin A was detected by UV at 326 nm and expressed in µg of Retinol Equivalent (RE) per 100 g.

Figure 1:
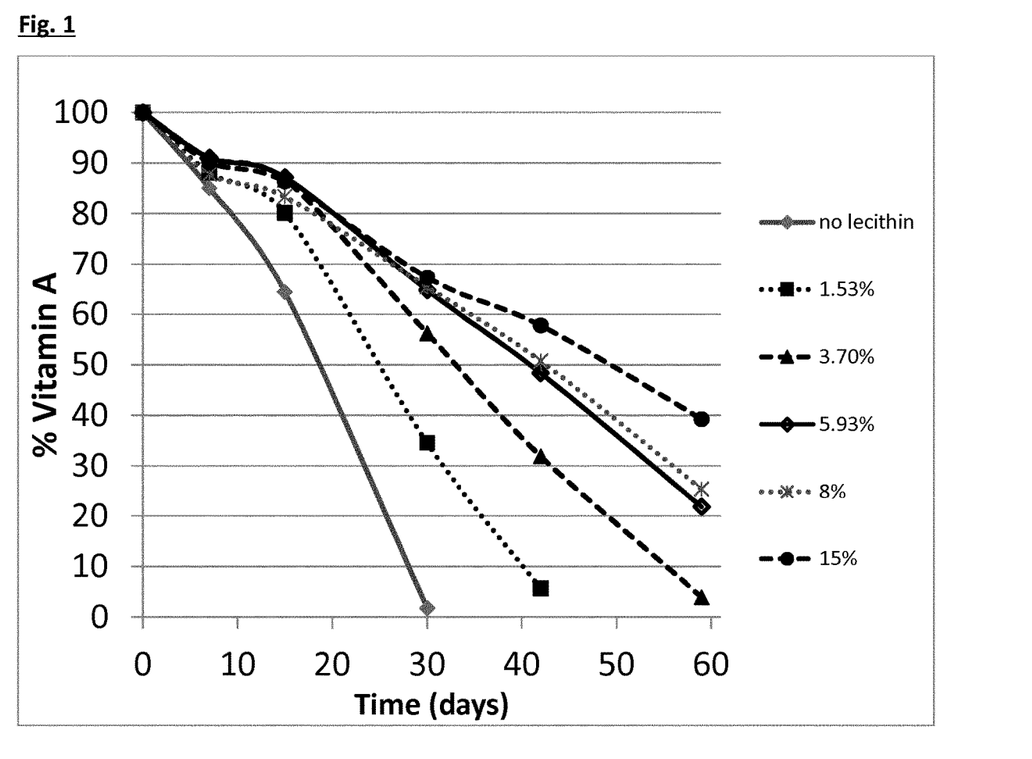
FIG. 1 shows the degradation of vitamin A palmitate (0.33 wt. %) in palm oil with different levels of lecithin at 60° C. and 68% RH.

The degradation curves are shown in FIG. 1. The mixtures containing lecithin at these levels comprised self-assembled structures (see Example 3). It can be seen that increasing the quantity of lecithin increases the stabilization of vitamin A until a lecithin level of 5.93%.

Example 2: Degradation of Vitamin A in Oil Under Different Conditions

Vitamin A mixtures in palm oil were prepared as in Example 1, the mixtures being:

| Mixture | Vitamin A palmitate (wt. %) | Lecithin (wt. %) | BHT (wt. %) |
|---|---|---|---|
| A | 0.1 | — | — |
| B | 0.1 | — | 0.06 |
| C | 0.1 | 5.93 | — |
| D | 0.33 | — | — |
| E | 0.33 | 5.93 | — |

Figure 2:
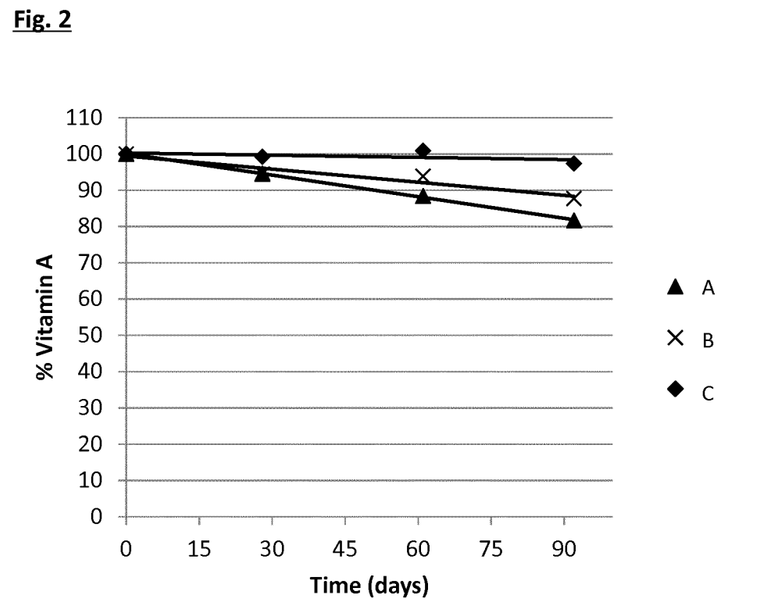
FIG. 2 shows vitamin A degradation curves at 40° C. and 68% RH for palm oil+0.1% vitamin A palmitate (A), palm oil+0.1% vitamin A palmitate+0.06 wt. % BHT (B) and palm oil+0.1 wt. % vitamin A palmitate+5.93 wt. % lecithin (C).
Figure 3:
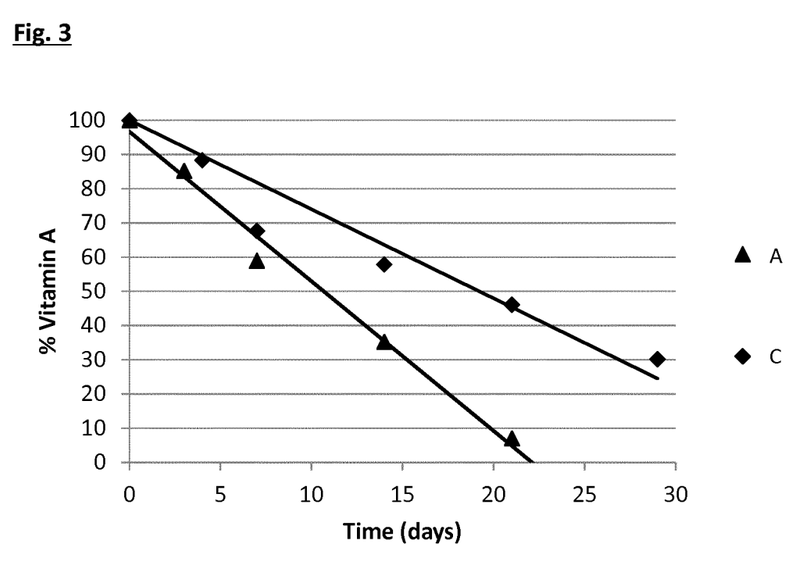
FIG. 3 shows vitamin A degradation curves at 80° C. and 68% RH for palm oil+0.1 wt. % vitamin A palmitate (A), palm oil+5.93 wt. % lecithin+0.1 wt. % vitamin A palmitate (C).
Figure 4:
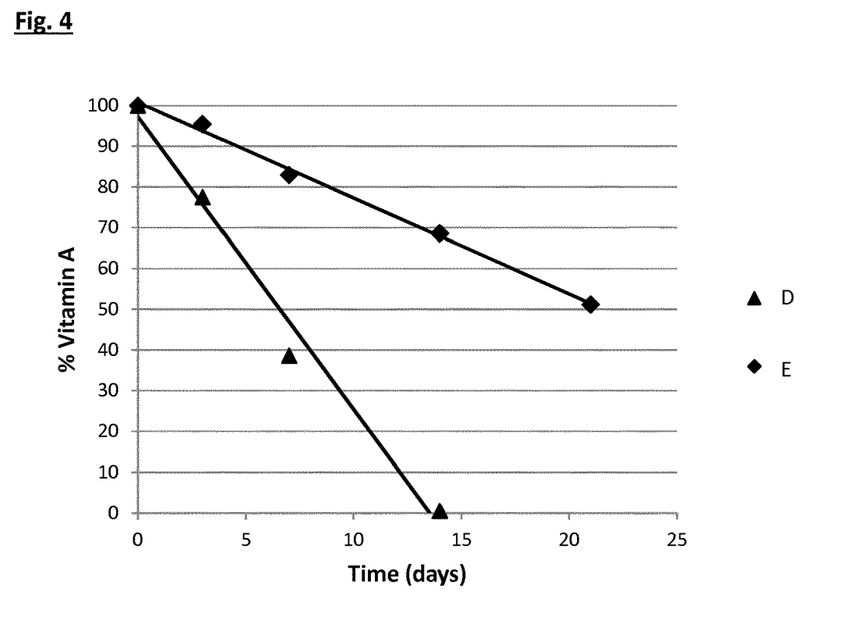
FIG. 4 shows vitamin A degradation curves at 75° C. and 50% RH for palm oil+0.33 wt. % vitamin A palmitate (D) and palm oil+5.93 wt % lecithin+0.33 wt. % vitamin A palmitate (E).

In the mixture where the antioxidant butylated hydroxytoluene (BHT) (Fluka) was present, the BHT was added with the vitamin A palmitate. The total amount of lipid was 500 g. For the storage tests three conditions were used with climatic chambers regulated at 40° C. and 68% relative humidity (FIG. 2: samples A, B and C), 80° C. and 68% relative humidity (FIG. 3: samples A and B) and 75° C. and 50% relative humidity (FIG. 4: samples D and E). Vitamin A analysis was performed as in Example 1. The degradation curves are shown in FIGS. 2, 3 and 4. The mixtures containing lecithin at this level comprised self-assembled structures (see Example 3). It can be seen that the lecithin self-assembled structures stabilize vitamin A at these conditions, and that lecithin self-assembled structures provides better stability than BHT.

Example 3: Observation of Self-Assembled Structures

Laboratory SAXS measurements were performed with a MicroMax-002+ microfocused X-ray machine (Rigaku), operating at 4 kW, 45 kV, and 0.88 mA. The Kα X-ray radiation of wavelength λ=1.5418 Å emitted at the Cu anode is collimated through three pinholes of respective sizes 0.4, 0.3, and 0.8 mm. The scattered intensity was collected on a two-dimensional Triton-200 X-ray detector (20 cm diameter, 200 µm resolution) for 16 h. The scattering wave vector is defined as $q=4\pi \sin(\theta)/\lambda$, where $2\theta$ is the scattering angle. The sample chamber used gives access to q ranges of 0.01 to 0.44 Å$^{-1}$. Silver behenate was used for q vector calibration. Scattered intensity data were azimuthally averaged using SAXSgui software (Rigaku). Samples were filled into 1.5 mm diameter quartz capillaries, sealed with epoxy glue (UHU). The X-ray machine is thermostated at 22.0±0.5° C., taken as room temperature.

Figure 5:
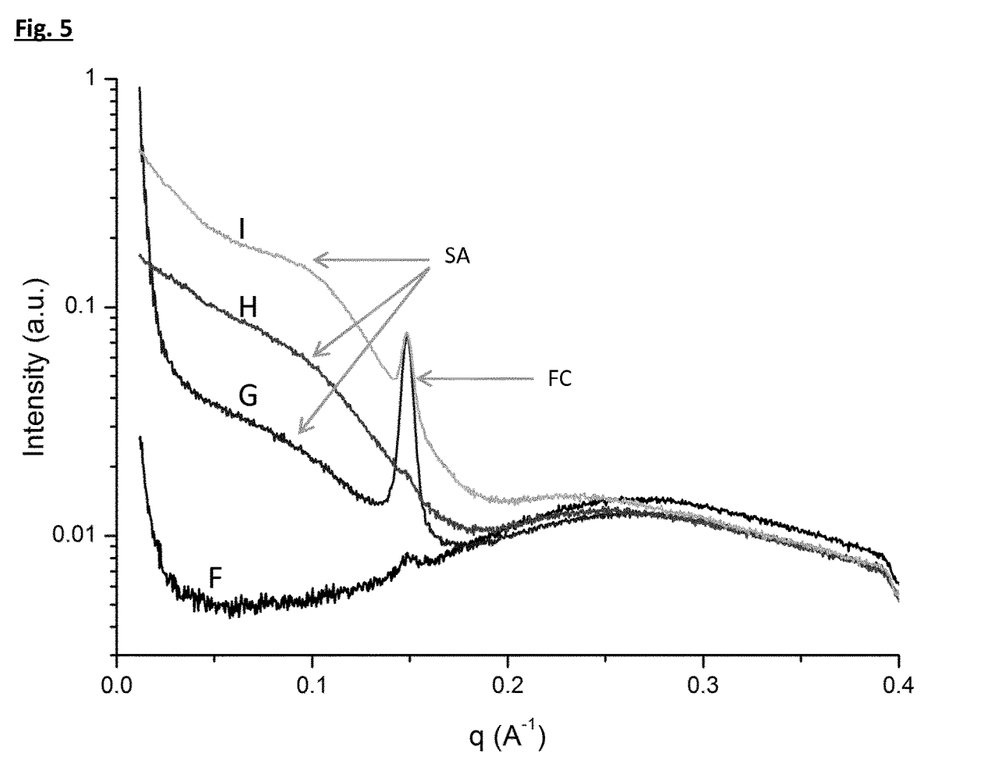
FIG. 5 shows small-angle X-ray scattering (SAXS) data at 30° C. of palm oil with the addition of lecithin at 0 wt. % (F), 2 wt. % lecithin (G), 6 wt. % lecithin (H) and 15 wt. % lecithin (I).
Figure 6:
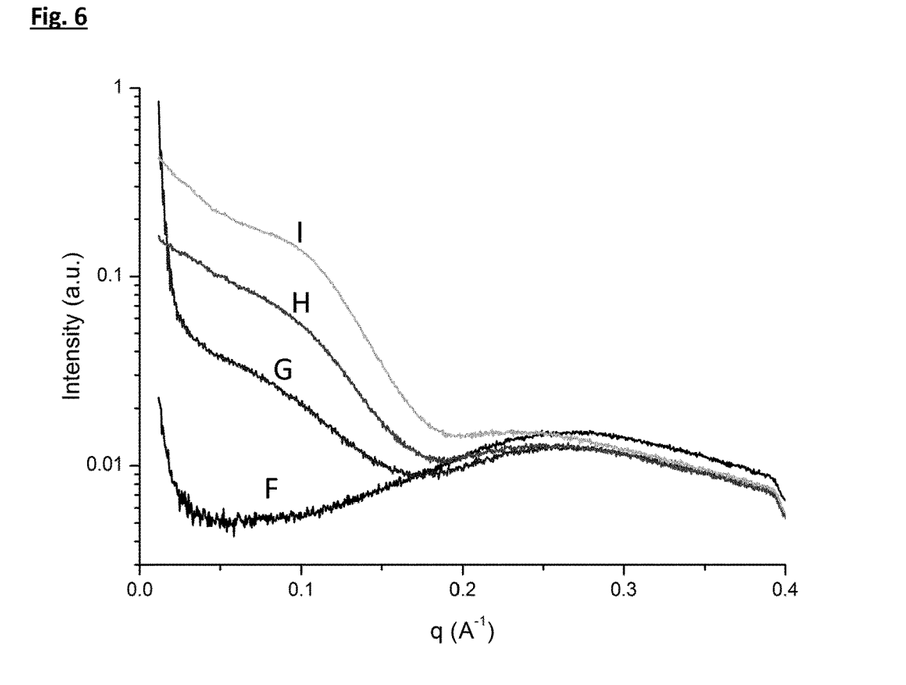
FIG. 6 shows SAXS data at 40° C. of palm oil with the addition of lecithin at 0 wt. % (F), 2 wt. % lecithin (G), 6 wt. % lecithin (H) and 15 wt. % lecithin (I).
Figure 7:
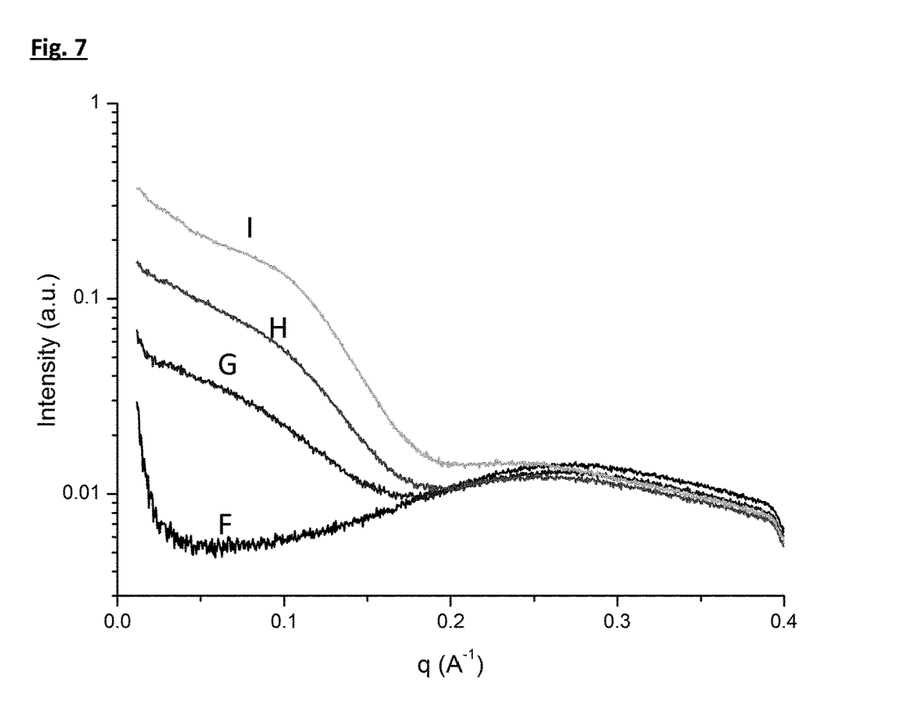
FIG. 7 shows SAXS data at 60° C. of palm oil with the addition of lecithin at 0 wt. % (F), 2 wt. % lecithin (G), 6 wt. % lecithin (H) and 15 wt. % lecithin (I).

Mixtures in palm oil were prepared with no lecithin (F), 2 wt. % lecithin (G), 6 wt. % lecithin (H) and 15 wt. % lecithin (I). SAXS analysis was performed at 30° C. (FIG. 5), 40° C. (FIG. 6) and 60° C. (FIG. 7). Self-assembled structures (reverse micelles) are confirmed to be present when lecithin is added by the presence of scattering peaks or humps (indicated as SA). At the lower temperature of 30° C. (FIG. 5), some crystallization of the fat (indicated as FC) can be observed.

Figure 8:
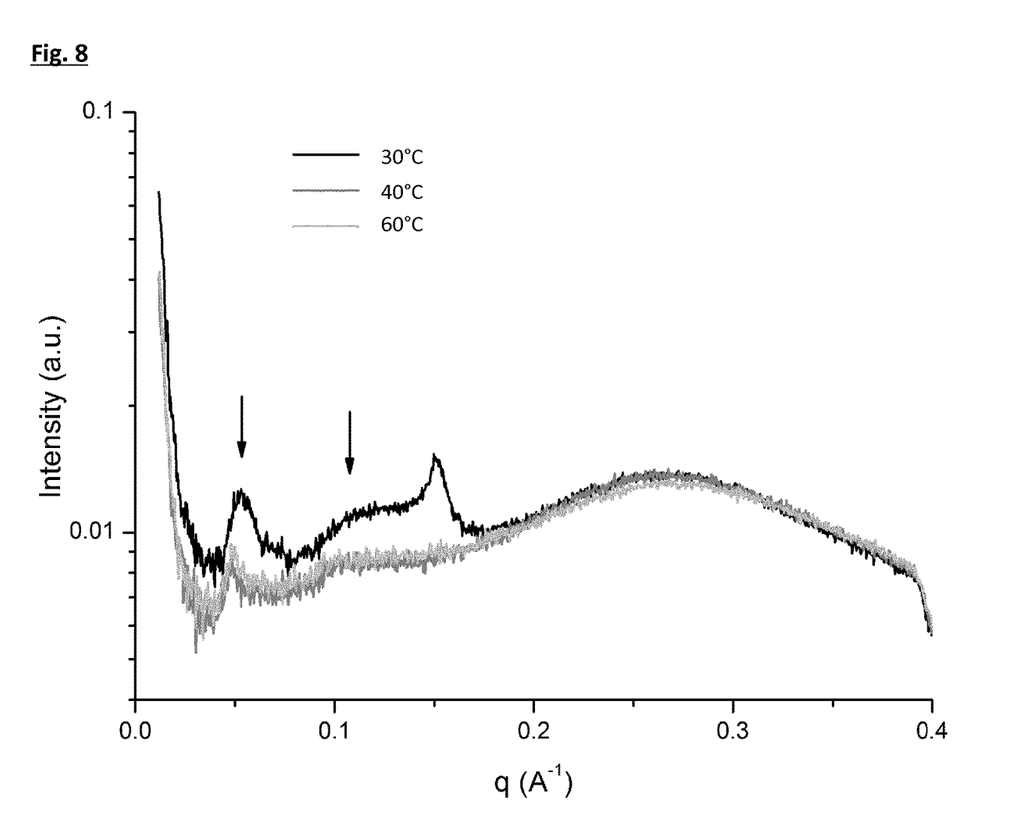
FIG. 8 shows SAXS data at 30° C., 40° C. and 60° C. for samples containing 6 wt. % lecithin and an excess of water showing the presence of self-assembled structures (reversed hexagonal).

Further mixtures in palm oil were prepared with 6 wt. % lecithin and an excess of water, where part of the water is solubilised in the self assembled structure (e.g. formed by lecithin and palm oil) and the rest of the water (the excess) forms a separate phase. SAXS data are shown in FIG. 8. The arrows indicate the presence of reversed hexagonal self-assembled structures.

Still further mixtures were prepared in sunflower oil (Florin) with lecithin and vitamin A palmitate.

| Mixture | Sunflower oil (wt. %) | Vitamin A palmitate (wt. %) | Lecithin (wt. %) |
| --- | --- | --- | --- |
| J | 98 | — | 2 |
| K | 97.67 | 0.33 | 2 |
| L | 100 | — | — |
| M | 98.17 | 0.33 | 1.5 |
| N | 99.17 | 0.33 | 0.5 |

Figure 9:
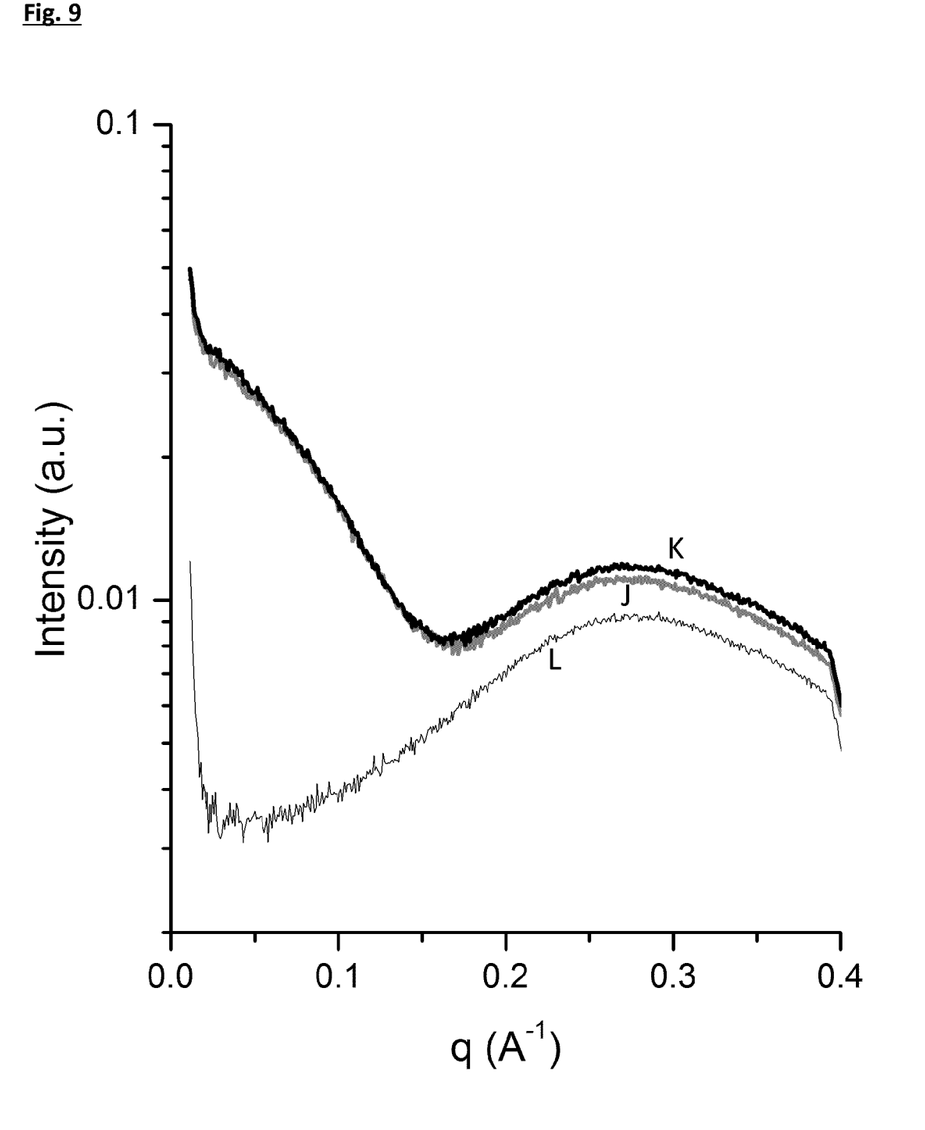
FIG. 9 shows SAXS data for samples containing sunflower oil and 2 wt. % lecithin (J), sunflower oil, 0.33 wt. % vitamin A palmitate and 2 wt. % lecithin (K) and pure sunflower oil (L).
Figure 10:
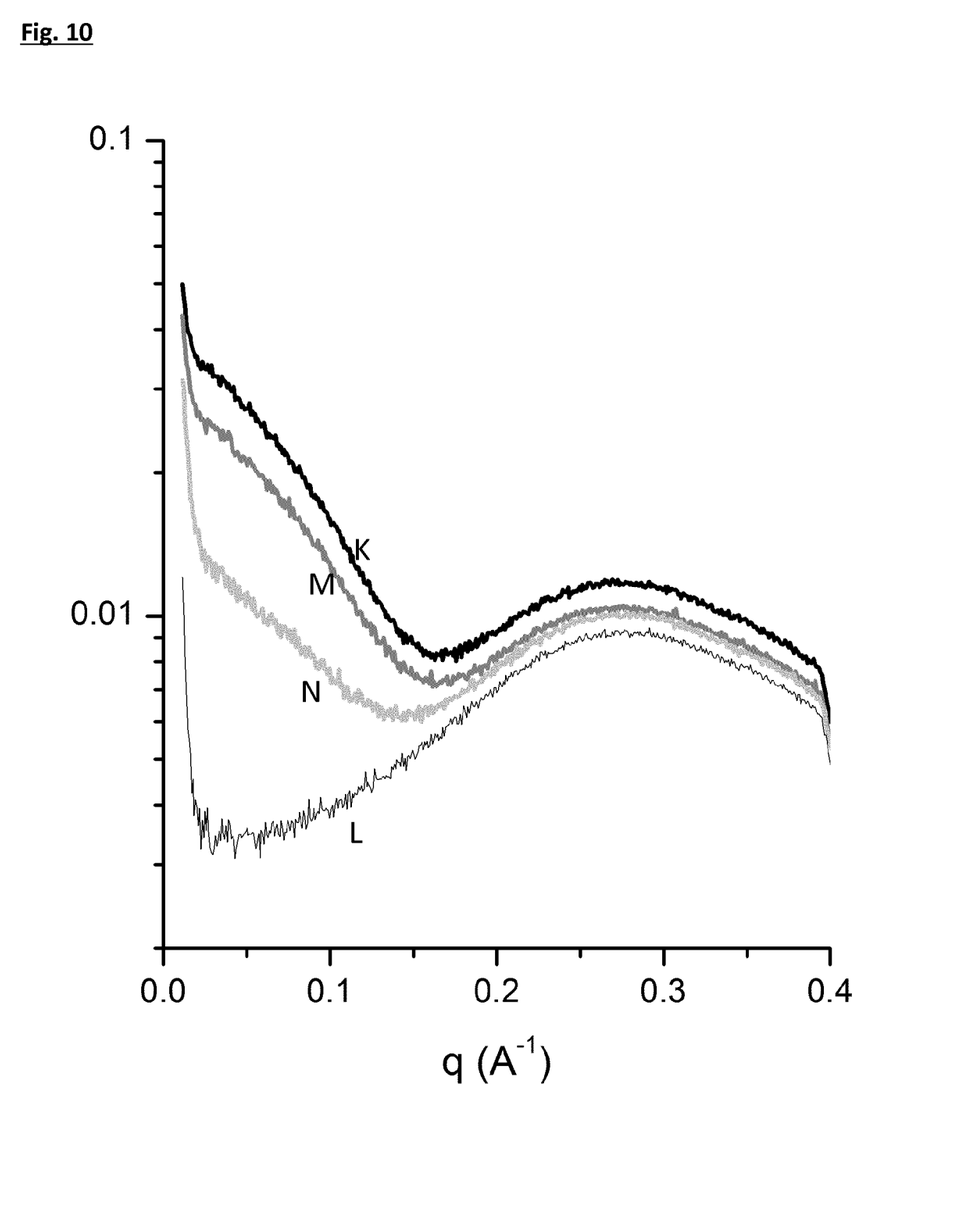
FIG. 10 shows SAXS data for samples containing sunflower oil and 2 wt. % lecithin (K), sunflower oil, 0.33 wt. % vitamin A palmitate and 1.5 wt. % lecithin (M), sunflower oil, 0.33 wt. % vitamin A palmitate and 0.5 wt. % lecithin (N) and pure sunflower oil (L).

The SAXS curves for the mixtures at 30° C. are shown in FIGS. 9 and 10. Micelles were observed in all the lecithin concentrations studied (e.g. down to 0.5 wt. %). The presence of vitamin A palmitate did not alter the formation of micelles.

Example 4: Degradation of Provitamin A

All-trans-β-carotene dispersed in sunflower oil (DSM) was used for preparing storage samples. The commercial dispersion consists of 60% sunflower oil, 30% crystalline all-trans-β-carotene, stabilized by 10% DL-α-tocopherol. The β-carotene was dissolved in high oleic sunflower oil (70-85% of oleic acid, 3-20% of linoleic acid and 3-5% of palmitic acid and stearic acid). The concentration of the β-carotene solution was set to 0.07 g/100 g oil, since the maximum solubility is at 0.08 g/100 g oil at ambient conditions.

The β-carotene was weighed and then oil was added. For one sample (P), 3 wt. % lecithin was added while the other sample (O) was without lecithin. The samples were stirred (IKA RET basic C) for 15 minutes and installed in an oven (Memmert) for 3 hours at 60° C. After the heat treatment approximately 30 g of sample was poured in each plastic storage container (diameter: 28 mm; height: 70 mm) and installed without a lid in a storage chamber at 60° C. and 45% RH. In total, 7 samples were taken including the initial sample (after 0 days) and the final sample (after 40 days).

Samples were analysed using a HPLC (high performance liquid chromatography) method coupled with UV detection, to analyse the quantity of trans-β-carotene, 9-cis-β-carotene and 13-cis-β-carotene. The limit of quantification is 50 μg/100 g and the detection limit is 20 μg/100 g. The standard deviation of the analysis method is 11%.

Figure 11:
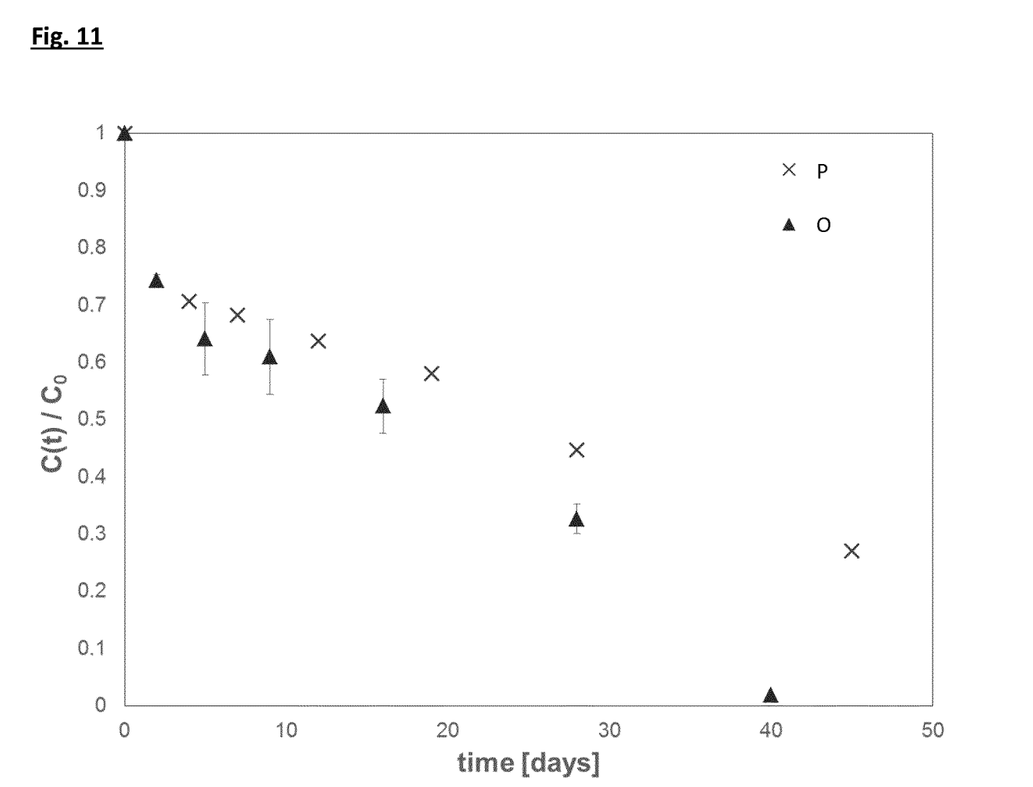
FIG. 11 shows the normalized concentration of trans-$\beta$-carotene in high oleic sunflower oil over time at 60° C., 45% RH with no lecithin (O) and 3 wt. % lecithin (P).

In FIG. 11, the normalized concentration of all-trans-β-carotene is shown over time. Since trans-β-carotene is the most active form of β-carotene only this isomeric form was quantified. It can be seen that the addition of 3 wt. % lecithin, so as to form self-assembly structures, stabilizes the β-carotene (a provitamin A).

Example 5: Degradation During Heating of Emulsions Containing Antioxidants

Palm oil and vitamin A palmitate were liquefied at 70° C. and 50° C. respectively in water baths. The time of immersion of vitamin A palmitate was kept as brief as possible to allow the sample to melt but not degrade. MiliQ water (250 ml per sample) was heated up at 85° C. in an oven. In a 25-mL Schott bottle, 0.0432 g of vitamin A palmitate and 12.9 g of palm oil were weighed. When applicable, lecithin (0.815 g), -tocopherol (0.008 g) or BHT (0.008 g) was added to the oil containing vitamin A palmitate. The resulting solutions were stirred for five minutes at 250 rpm in a 50° C. water bath.

Emulsions were dispersed using a Polytron® PT 3100 (Kinematica AG). The Polytron was pre-heated in a 400 ml beaker containing hot water (to avoid the oily phase of the emulsion sticking to the equipment). The bottom of another 400 ml beaker was dug into a 50° C. water bath for 30 seconds. The beaker was subsequently dried and placed on a balance. Then, 0.1295 g (without lecithin) or 0.1375 g (with lecithin) of master solution prepared above was weighed in the hot beaker, avoiding the oil crystallizing in the recipient. A volume of 250 ml of hot MiliQ water was added to the beaker. The resulting solutions were subjected to the Polytron for 5 minutes at 17,000 rpm. This resulted in an emulsion with particle size having a $d_{[3,2]}$ of 3.3 μm as determined by light scattering using Malvern Mastersizer 2000. Five aliquots of 15 g of the above emulsions were weighed in Pyrex culture tubes. The five tubes were closed and three of them were placed into heating blocks preheated at 98° C. to simulate simmering during cooking. One aliquot was taken out of heating block each 30 minutes and cooled down for 2 minutes in water at room temperature. The two remaining tubes correspond to a replicate of $T_0$, not heated. A volume of 13.7 μl of Tween 20 was added to each tube to stabilize the emulsion until analysis. All tubes were vortexed for 10 seconds and then incubated at 4° C. in a fridge before proceeding with analysis. All experiments were repeated at least twice.

Figure 12:
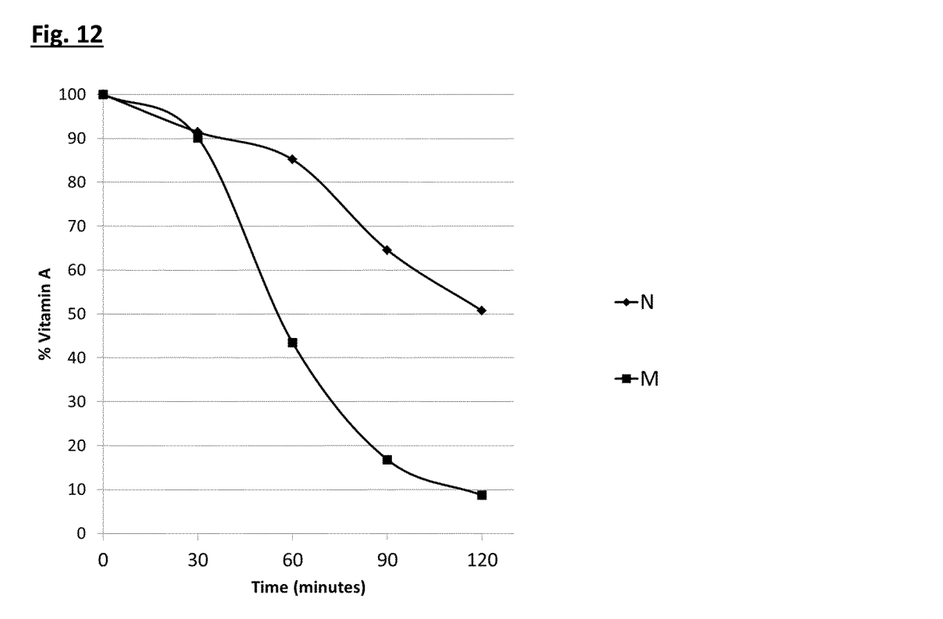
FIG. 12 shows vitamin A degradation curves at 98° C. in excess water for emulsions of palm oil+0.33% vitamin A palmitate+0.067 wt. % tocopherol+5.93 wt. % lecithin (M) and palm oil+0.33% vitamin A palmitate+0.067 wt. % BHT+5.93 wt. % lecithin (N).

All samples contained 0.33% vitamin A palmitate in oil. Sample M contained 5.93 wt. % lecithin and 0.067 wt. % -tocopherol and sample N contained 5.93 wt. % lecithin and 0.067 wt. % BHT. The degradation of vitamin A in the samples is shown in FIG. 12. The combination of BHT with lecithin self-assembled structures was surprisingly found to be considerably more effective at stabilizing vitamin A under conditions of simmering than the combination of -tocopherol with lecithin self-assembly structures.

Example 6: Concentrated Bouillon with Vitamin A

A hard, herb bouillon tablet has the following composition:
47% milled salt
20% milled monosodium glutamate
13% maltodextrin with a DE value of 50
11.245% olive oil
6.5% dehydrated powdered aromatics and spices
1.4% water containing plant extract solution (70% water)
0.1% dried herbs (e.g. thyme or oregano)
0.71% lecithin
0.038% vitamin A palmitate
0.007% BHT The production process comprises the following steps: The olive oil and vitamin A palmitate are liquefied at 60° C. and then lecithin and BHT is added before stirring the resulting mixture for five minutes at 50° C. The resulting olive oil mixture contains vitamin A, lecithin and self-assembled structures. The plant extract solution is then emulsified with the olive oil mixture in a high pressure homogeniser. The emulsion is then atomised onto a premix of the powdered ingredients in a ploughshare mixer fitted with a chopper. The dried herbs are added at the end. The mixture thus obtained is tableted under a pressure of 10-150 bar. A similar bouillon tablet may be produced with vitamin A acetate replacing vitamin A palmitate. The 0.007% BHT in the formulation may be replaced by with 0.15% GT-FORT 101 SF Liquid [Kemin Industries, Des Moines, USA] (green tea extract); or 0.15% FORTIUM R20 Liquid [Kemin Industries] (rosemary extract); or 0.15% NaturFORT 15 L Liquid [Kemin Industries] (rosemary extract and green tea extract); or 0.03% ascorbyl palmitate obtained from DSM.

The vitamin A in the product obtained has good stability, both during storage and when cooked in water.

Example 7: Degradation of Vitamin A in Sunflower Oil in the Presence and Absence of Lecithin Vitamin A mixtures in high oleic sunflower oil (Sabo) were prepared as in Example 1, where high oleic sunflower oil replaces palm oil. The prepared mixtures were as follows:

| Mixture | Vitamin A palmitate (wt. %) | Lecithin (wt. %) |
|---|---|---|
| F | 0.33 | — |
| G | 0.33 | 5.93 |

Figure 13:
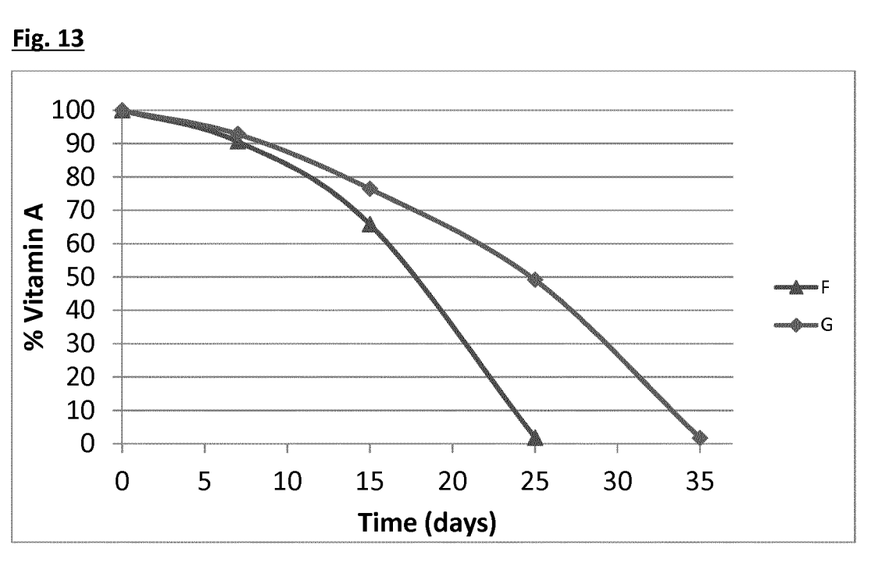
FIG. 13 shows vitamin A degradation curves at 60° C. and 68% RH for high oleic sunflower oil+0.33 wt. % vitamin A palmitate (F) and high oleic sunflower oil+0.33 wt. % vitamin A palmitate+5.93 wt. % lecithin (G).

Vitamin A analysis was performed as in Example 1. The degradation curve is shown in FIG. 13. The mixtures containing lecithin at these levels comprised self-assembled structures (see Example 3). It can be seen that the lecithin self-assembled structures can also stabilize vitamin A in high oleic sunflower oil.

Example 8: Degradation of Vitamin A During Heating of Emulsions Containing Natural Antioxidants Vitamin A mixtures were prepared as in Example 5. When applicable, green tea extract (0.021 g), rosemary extract (0.021 g), ascorbyl palmitate (0.004 g), rosemary extract+ green tea extract (0.021 g) or BHT (0.008 g) were added to the oil containing vitamin A palmitate and lecithin. After emulsion preparation, only two aliquots of 15 g were prepared. One of them was placed into heating blocks preheated at 98° C. to simulate simmering during cooking. This aliquot was taken out of heating block after 80 minutes and cooled down for 2 minutes in water at room temperature. The remaining tube corresponds to $T_0$, not heated. As in example 5, a volume of 13.7 µl of Tween 20 was added to each tube. All tubes where then incubated at 4° C. before proceeding with analysis.

All samples contained 0.33% vitamin A palmitate in oil. Sample Q contained 5.93 wt. % lecithin. Sample R contained 5.93 wt. % lecithin and 0.15% green tea extract. Sample S contained 5.93 wt. % lecithin and 0.15% rosemary extract. Sample T contained 5.93 wt. % lecithin and 0.03% ascorbyl palmitate. Sample U contained 5.93 wt. % lecithin and 0.15% of a 1:1 mixture of rosemary extract and green tea extract. Sample V contained 5.93 wt. % lecithin and 0.067% BHT.

The degradation of vitamin A in the samples is shown in the table below. The combination of lecithin with natural antioxidants such as rosemary extract, green tea extract, a combination of both or ascorbyl palmitate was found to be effective at stabilizing vitamin A under conditions of simmering than in the absence of antioxidants. The combination of lecithin, rosemary extract and green tea extract was almost as good as the stabilizing effect of synthetic antioxidant BHT. The analysis of vitamin A was performed as in Example 1.

| Mixture | Remaining Vitamin A after 80 minutes cooking at 98° C. |
|---|---|
| Q | 5.53% |
| R | 10.86% |
| S | 12.21% |
| T | 15.60% |
| U | 29.24% |
| V | 44.20% |

The table shows remaining Vitamin A palmitate quantity after cooking of oil in water emulsions at 98° C. for 80 minutes. Percentages are related to oil. The palm oil used was of a lower quality than the one used in Example 5 so the results are not directly comparable with FIG. 12.

The invention claimed is:

1. A process for preparing a stabilized vitamin A or provitamin A composition, the process comprising:
   providing triglycerides, lecithin, and at least one liquid compound selected from the group consisting of vitamin A and provitamin A; and
   mixing the triglycerides, the lecithin and the at least one compound to form the stabilized vitamin A or provitamin A composition,
   wherein the stabilized vitamin A or provitamin A composition consists of the triglycerides, the lecithin, the at least one compound, and water;
   the triglycerides are at least 50 wt. % of the total weight of the stabilized vitamin A or provitamin A composition;
   the lecithin is 0.1-30 wt. % based on the amount of the triglycerides; and
   the stabilized vitamin A or provitamin A composition has a water content between 0.001 wt % and 4 wt. % of the total weight of the stabilized vitamin A or provitamin A composition.

2. The process according to claim 1, wherein at least a portion of the lecithin forms self-assembled structures having a reversed micellar cubic structure.

3. The process according to claim 1, wherein at least part of the at least one compound is dissolved in the triglycerides.

4. The process according to claim 1, wherein the process further comprises adding and mixing an antioxidant to the stabilized vitamin A or provitamin A composition.

5. The process according to claim 4, wherein the antioxidant is selected from the group consisting of rosemary extract, green tea extract, a butylated phenol and combinations thereof.

6. The process according to claim 1, wherein the stabilized vitamin A or provitamin A composition has a water activity greater than 0.3.

7. The process according to claim 1, wherein the surfactant is 0.5-6 wt. % of the stabilized vitamin A or provitamin A composition.

8. The process according to claim 1, wherein the at least one compound is at least 0.1 wt. % of the stabilized vitamin A or provitamin A composition.

9. The process according to claim 2, wherein the triglycerides form an oil phase of the stabilized vitamin A or provitamin A composition, and the self-assembled structures are in the oil phase.

10. The process according to claim 2, wherein the self-assembled structures are at least 0.05 wt. % of the stabilized vitamin A or provitamin A composition.

11. The process according to claim 1, wherein the stabilized vitamin A or provitamin A composition is an emulsion.

* * * * *